United States Patent
Stupperich et al.

(10) Patent No.: US 7,482,505 B2
(45) Date of Patent: Jan. 27, 2009

(54) SINGLE-USE HYGIENE ARTICLE

(75) Inventors: Hans-Peter Stupperich, Heidenheim (DE); Wolfgang Röhrl, Herbrechtingen (DE)

(73) Assignee: Paul Hartmann AG, Heidenheim (DE)

( * ) Notice: Subject to any disclaimer, the term of this patent is extended or adjusted under 35 U.S.C. 154(b) by 0 days.

(21) Appl. No.: 10/556,187

(22) PCT Filed: May 12, 2004

(86) PCT No.: PCT/EP2004/005053

§ 371 (c)(1),
(2), (4) Date: Nov. 9, 2005

(87) PCT Pub. No.: WO2004/105668

PCT Pub. Date: Dec. 9, 2004

(65) Prior Publication Data

US 2006/0282053 A1 Dec. 14, 2006

(30) Foreign Application Priority Data

Jun. 2, 2003 (DE) ................................ 103 26 022

(51) Int. Cl.
*A61F 13/15* (2006.01)
*A61F 13/20* (2006.01)

(52) U.S. Cl. .............. 604/378; 604/385.01; 604/385.21; 604/385.101; 604/385.27

(58) Field of Classification Search .................. 604/367, 604/385.01, 385.101, 385.12, 385.16, 385.23
See application file for complete search history.

(56) References Cited

U.S. PATENT DOCUMENTS 4,410,324 A  10/1983  Sabee
4,413,996 A  11/1983  Taylor
4,834,735 A * 5/1989  Alemany et al. ............ 604/368
5,462,541 A  10/1995  Rasmussen (Continued)

FOREIGN PATENT DOCUMENTS

DE         40 16 864        6/1991

(Continued)

*Primary Examiner*—Michele Kidwell
(74) *Attorney, Agent, or Firm*—Paul Vincent

(57) ABSTRACT

The invention relates to a single use hygiene article, comprising an absorbing body layer (24, 60, 70), which serves to store body fluids and which can also contain superabsorbent materials, and comprising standing cuff elements (26, 28), which extend in an essentially longitudinal direction, form a lateral leakage barrier and which are attached to the body-facing side of the article at least along a cuff base line (34, 36; 62, 64; 76, 78). The cuff elements (26, 28) are guided with variable distances between the cuff base lines (34, 36; 62, 64; 76, 78). The aim of the invention is to improve the absorption characteristics of the hygiene article. Towards this end, the article is designed in such a manner that the absorbing body layer (24, 60, 70) comprises, in a transversal direction (44) of the hygiene article up to the lateral edges (16) and/or in a longitudinal direction (38) up to at least one longitudinal end (40), an increasing mass per unit area of an absorbent material of this layer. In addition, the area (46, 56, 74) of the greater mass per unit area has at least one partial area (48, 66) in which the distance (42) of the cuff base lines (34, 36; 62, 64; 76, 78) from one another is greater that outside this partial area (48, 50, 66, 68).

17 Claims, 3 Drawing Sheets

U.S. PATENT DOCUMENTS

| | | | |
|---|---|---|---|
| 5,624,423 A | 4/1997 | Anjur | |
| 5,769,838 A * | 6/1998 | Buell et al. | 604/396 |
| 5,843,067 A | 12/1998 | Darby | |
| 6,117,121 A * | 9/2000 | Faulks et al. | 604/385.29 |
| 6,498,283 B1 | 12/2002 | Wada | |
| 2003/0023225 A1 | 1/2003 | Sayama | |

FOREIGN PATENT DOCUMENTS

| | | |
|---|---|---|
| DE | 692 29 828 | 4/2000 |
| EP | 1 293 186 | 3/2003 |
| WO | 93/31952 | * 11/1995 |
| WO | WO 01/05440 | 1/2001 |

* cited by examiner

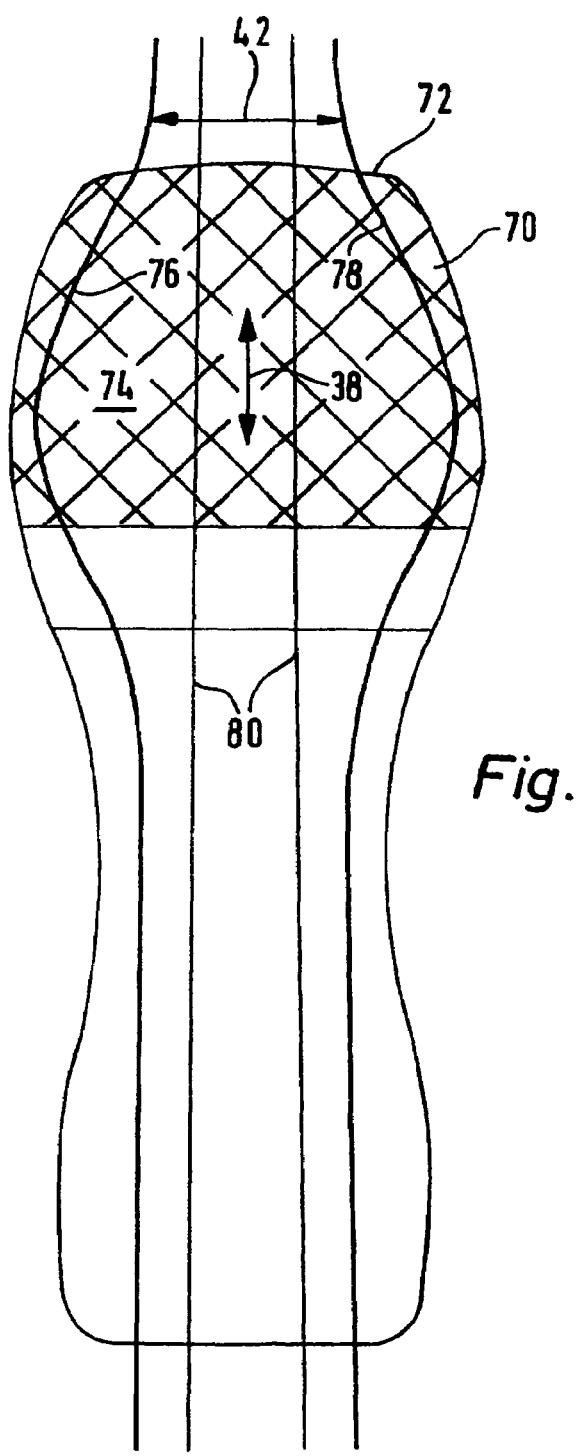
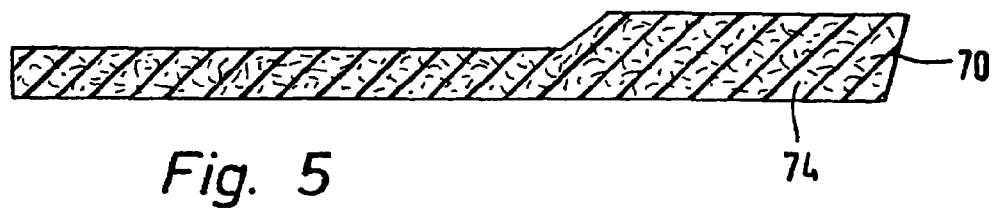
Fig. 4
Fig. 5

SINGLE-USE HYGIENE ARTICLE

This application is the national stage of PCT/EP2004/005053 filed on May 12, 2003 and also claims Paris Convention priority of DE 103 26 022.6 filed on Jun. 2, 2003.

BACKGROUND OF THE INVENTION

The invention concerns a single use hygiene article having an absorptive body layer suitable for long term storage of body fluids which may contain super-absorbing materials and with cuff elements forming a sideward discharge blockage which are substantially disposed in a longitudinal direction at least through sections and which are attached, at least along a cuff base line, to the side of the article facing the body of the user, wherein the cuff elements are guided at variable separations from each other with respect to their cuff base lines. The invention also concerns a diaper or diaper pants and incontinence inlays or incontinence diapers or pants. A hygiene article of this type is e.g. described in EP0751756B1. In this hygiene article, the cuff elements or their cuff base lines follow the hour glass shape of the absorptive body.

EP0254476B1 discloses an absorptive body structure having a central liquid retention zone of reduced density and reduced surface density which is at least partially surrounded by a storage zone of higher density and higher surface density. This is intended to increase the capacity for fluid retention as well as distribution in particular in the case of liquid floods. A similar teaching is disclosed by EP1006970B1.

Departing therefrom, is the fundamental purpose of the present invention to create a hygiene article which is well suited, in particular in the event of flooding of liquids, to prevent sideward leakage and to assure that the incident liquid is rapidly absorbed and stored for a long period of time in the absorbing structure and in the absorptive body layer.

SUMMARY OF THE INVENTION

This purpose is achieved in accordance with the invention with a hygiene article of the above mentioned kind in that the absorptive layer has a surface density of absorbing material which increases in a transverse direction of the hygiene article towards the side edges and/or in the longitudinal direction towards at least one longitudinal end, wherein the region of increased surface density has at least one partial region in which the separation between the cuff base lines with respect to each other is larger than outside of this partial region.

In accordance with the invention, it has been discovered that the cuff elements can be guided at variable cuff base line separations. For example, in the forward region or in the rear region, i.e. outside of the crotch region of the hygiene article, the lines are further separated from each other thereby leading to an increase surface area which is available for the retention of fluids in particular in the case of flooding fluid loading on the surface of the hygiene article with the fluids being distributed between the elevated cuff elements. It has turned out to be advantageous for rapid fluid absorption when the absorbing area is chosen to be as large as possible. However, this has the consequence that the cuff elements and the pockets built thereby for the retention of body discharges are located in the region of the edge of the absorptive material where the absorptive capacity could be insufficient or, due to interactions with the edge of the absorptive body, an insufficient sealing or retention capacity is present. Moreover, the fixation of the cuff elements to the materials of the hygiene article can cause undesired capillary transport of the fluid towards the edges of the hygiene article should insufficient absorption capacity be available. The current invention therefore recognizes that, by increasing the surface density of the absorbing material of the absorptive body precisely at those locations where the separation between the cuff base lines is maximized compared to other areas, improved and more reliable liquid retention properties of the hygiene article can be achieved. This increase in the surface density can be provided in a transverse direction towards the side edges so that both transverse sides outside of the central region have higher surface densities than in the central region. The increase in surface density can thereby be effected continuously or discontinuously.

An increased surface density can also be provided in the longitudinal direction towards at least one longitudinal end of the hygiene article. This leads to an increase surface density in the front region and/or in the rear region compared to the middle region, wherein, in accordance with the invention, at least a partial region of the regions of increased surface density has separations between the cuff base lines which are larger than outside of this partial region.

It has therefore been discovered in accordance with the invention that the guidance of the cuff elements and the cuff base lines advantageously creates a larger fluid retention capacity region in areas of larger separation between the cuff base lines to create a higher absorption capacity for permanent or long term storage of body fluids in the absorptive body layers and in the region of the cuff base lines.

Although the concepts in accordance with the invention can also be utilized in the middle, crotch region of the hygiene article, it has turned out to be particularly advantageous when the above mentioned partial regions are located outside of the middle longitudinal section in either a front and/or in a rear region of the hygiene article. In these locations of the hygiene article, the absorptive body structure in the transverse direction is more easily configured than in the crotch region. Since the functionability of the hygiene article should also be guaranteed for users who are prone or sleeping, the front region and the rear region are more important for liquid retention than has been assumed up to this point in time. Although "boy" diapers have been proposed having increasing 7 absorptive capacity in the front region, this absorptive capacity was centrally located i.e. in the middle region. In accordance with the present invention, an increased storage capacity is achieved by the cuff base lines through an increased surface density of absorptive material for long term storage of body fluids using an absorptive body layer which has a maximum separation between the cuff base lines.

In accordance with a further preferred embodiment of the invention, the cuff line elements are guided in such a fashion that the separation between the cuff base lines in the longitudinal direction has at least one maximum and preferably has a maximum in both the forward as well as in the rear region of the hygiene article. The reference hereto to passage through a maximum means that the separation between the cuff base lines increases in the longitudinal direction up to a maximum value and then once more decreases, i.e. the cuff base lines once more approach each other.

The cuff elements themselves include such materials which are conventionally used to form discharge blockings such as fleece materials for example card web, spun or melt blown fleece materials in particular fleece material laminates which includes spin(S) and melt blown (M) fleece layers in particular SM, SMS, SMMS fleece layer. Hydrophobic materials are preferentially used. However, cuff elements made from foils or foam materials can also be used.

In order to configure the absorptive body layer whose surface density can increase in the transverse direction and/or in the longitudinal direction there are no particular requirements which deviate substantially from those of usual absorptive body materials for long term storage of body fluids. One can thereby use a layer of pure fiber material in particular fluffed cellulose fibers which are suitable for long term storage of liquids due to there hydrophobility. Moreover, one can use synthetic in particular thermoplastic fibers optionally mixed with cellulose fibers. It has been particularly advantageous when the absorptive body structure includes super-absorbing materials in particular particle shaped super-absorbing materials. The absorptive body materials preferentially include a homogenous mixture of fibers and particle shaped super-absorbing materials. The absorptive body layer can furthermore be made from foam materials or include such materials.

In accordance with an embodiment of the invention, the base lines of the cuff elements which extend on both sides join each other in the front region and/or in the rear region. In this case, a pocket is created which seals in the longitudinal direction for the absorption of body discharge. The cuff elements themselves will then be preferentially configured in such a fashion that their distal ends touch each other or overlap. In this fashion a type of window opening is created.

Alternatively it would also be conceivable and particularly advantageous with regard to manufacturing considerations if the socket,lines of the cuff elements extending on both sides are separated from each other in the front region and/or in the rear region and extend up to the longitudinal end of the hygiene article at a separation with respect to each other.

In a further precise embodiment of the concept in accordance with the invention, the hygiene article is configured in such a fashion that the surface density of the absorptive body layer, or one of the absorbing materials, increases in the transverse or longitudinal directions by 30 to 200%, in particular by 30 to 150%, and preferentially by 50 to 120%.

In accordance with a preferred embodiment of the invention, the surface density of absorbing material of the absorbing body layer outside of said partial region assumes values of 200-500 g/m$^2$, in particular 250-450 g/m$^2$ and preferentially 280-350 g/m$^2$. In the partial region, it assumes values of 250-1000 g/m$^2$, in particular 350-750 g/m$^2$ and preferentially 500-700 g/m$^2$. The absorbing material of the absorptive body layer can be formed from fiber components in particular fluffed cellulose fibers.

Further, in particular, fluid retaining or storing absorptive body components can be provided above and/or below the absorptive body layer. For example, a preferentially open pored liquid retaining layer can be provided which is, however, preferentially not used for long term storage, rather only for acceptance and distribution of the liquid. A further preferentially SAP free layer disposed below the above mentioned absorptive body layer has also turned out to be advantageous. This layer serves as a substrate, in particular, to prevent escape of the grainier super-absorbing particle materials from the absorptive body layer.

In accordance with a particularly preferred embodiment of the present invention, the cuff elements are formed from tracks or track sections extending in the longitudinal direction. When these tracked sections define a desired dependence of the associated cuff base lines, the cuff elements are configured in such a fashion that the separation of a distal end of the elevated cuff elements from the corresponding cuff base line becomes larger the greater the separation of the cuff base lines from each other. This is also advantageous, since an increased effective height can be assumed in the widely extended, receiving regions of the elevated cuff elements. In a further improvement of the inventive concept, the separation of a distal end of the elevated cuff elements from the cuff base line within the above mentioned partial region advantageously has an increase surface density than outside of this partial region.

It has turned out to be advantageous and practical, when the separation between the distal end of the elevated cuff element from the cuff base line within the above mentioned partial region has values of 40-60 mm. The separation is therefore understood as an effective length in the event of flat cuff elements. The separation is preferentially 30-40 mm outside of the above mentioned partial region.

Further features, details and advantages of the invention can be extracted from the figures and the following description of preferred embodiments.

BRIEF DESCRIPTION OF THE DRAWING

FIG. 4 shows a plan view of an absorptive body of an additional embodiment with indicated dependence of the cuff base line; and FIG. 5 shows longitudinal side view of the absorptive body of FIG. 3.

DESCRIPTION OF THE PREFERRED EMBODIMENT

Figure 1:
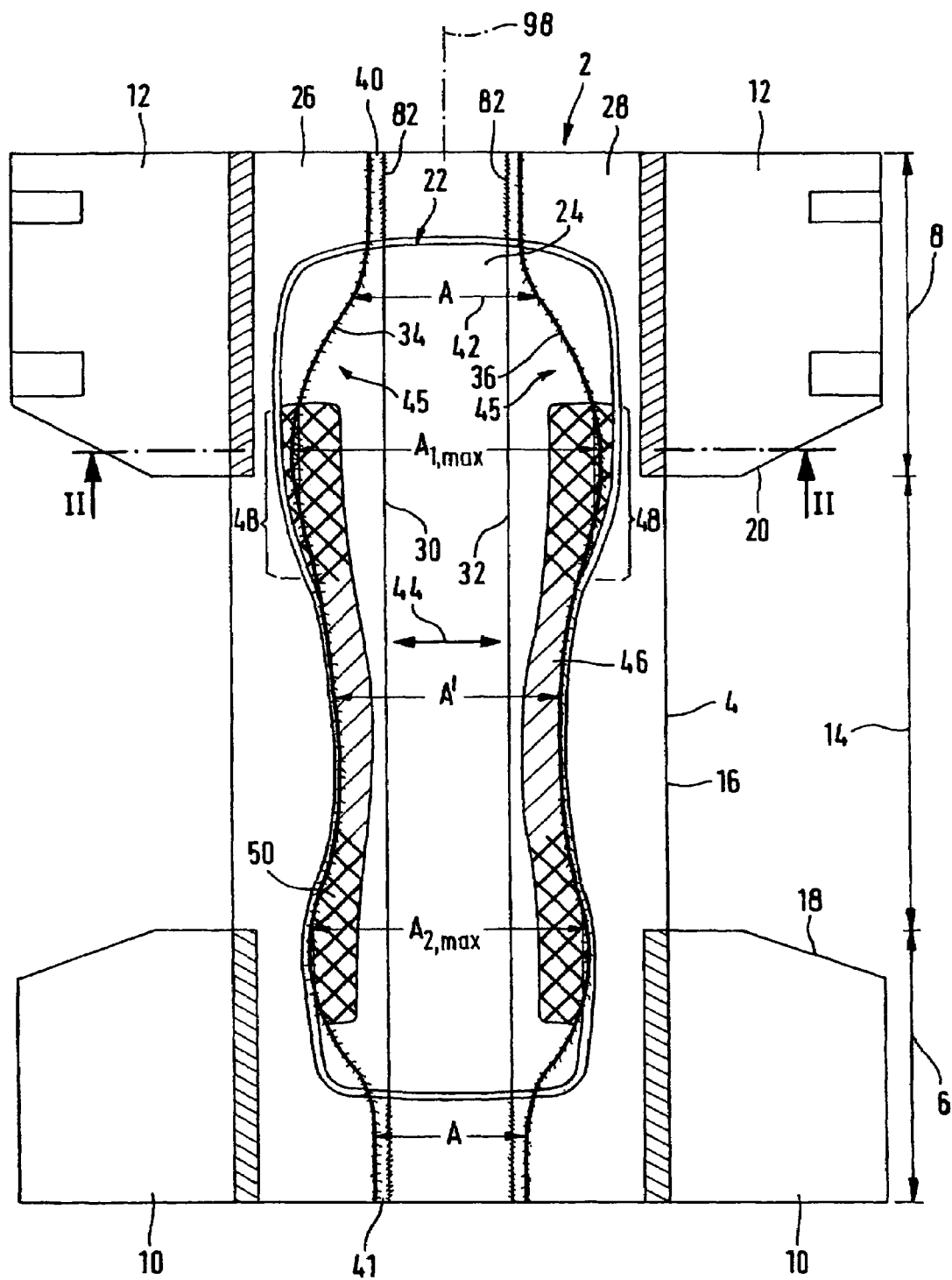
FIG. 1 show a plan view of a preferred embodiment of a hygiene article in accordance with the invention.
Figure 2:
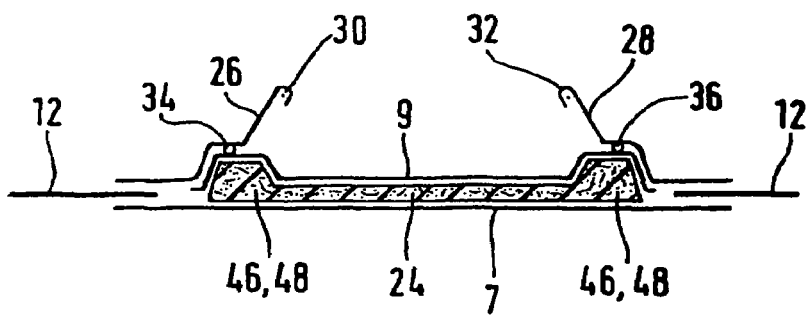
FIG. 2 shows a cut through the hygiene article according to FIG. 1 in the cut plane II-II of FIG. 1.

FIG. 1 shows a plan view of the side of a hygiene article facing the body of the user and indicated in its totality with reference symbol 2 in the form of an incontinence diaper in the flat state. FIG. 2 shows a corresponding section in the section plane along line II-II of FIG. 1. The hygiene article 2 includes a diaper chassis having side flaps 10 or 12 directly or indirectly introduced on both sides of a forward region 6 and a rear region 8. The region between the front region 6 and the rear region 8 is designated as a crotch region 14. A sideward edge 16 of the diaper body 4 in the crotch region together with the immediately adjacent side edges 18, 20 of the side flaps 10 and 12 define the leg openings of the user in the state of use of the hygiene article.

The chassis has a liquid impermeable layer 7 on its side facing away from the body of the user, whereas the side flaps 10, 11 are made from an actively breathing material, preferably an air permeable fleece material.

The hygiene article 2 also includes an absorptive body 22 and an open pore liquid retaining or distribution layer which only partially covers the absorptive body (not shown). The absorptive body 22 also includes an absorptive body layer 24 serving for long term storage of body fluids, which will be described more closely below. The absorptive body layer 24 seats on a thin layer made from fluffed cellulose (not shown in FIGS. 1 and 2) which has a uniform surface density of approximately 140 g/m$^2$.

Cuff elements 26, 28 extend in a longitudinal direction at least in the crotch region in an elevated fashion and have free distal edges 30, 32 which are preferentially provided with an elastic means. In order to prevent the cuff elements from folding over in an outward direction, the distal edges 30, 32 in the rear and forward regions are equipped with inwardly disposed attachments on the upper side of the hygiene articles using conventional procedures such as gluing or welding. The cuff elements 26, 28 are also introduced along each of the corresponding cuff base lines 34, 36 on the upper side of the hygiene article 2 and are, in particular, connected to at least one top sheet layer 9 (FIG. 2) which substantially covers the chassis 4.

The cuff base lines 34, 36 extend, as do the cuff elements, in the longitudinal direction 38 of the hygiene article. However, they are not parallel with respect to that longitudinal direction 38, rather are guided with varying separation between the cuff base lines 34, 36.

Departing from the longitudinal end 40 of the hygiene article 2, the cuff base lines 34, 36 initially extend precisely parallel to the longitudinal direction 38 at a separation 42 designated by value A. Within the rear region 8, the cuff base lines 34, 36 then proceed continuously in an arched-shaped fashion towards the outside so that their separation 42 continuously increases up to a maximum value $A_{1max}$. The separation then decreases continuously from the value $A_{1max}$ through a value A' in the: crotch region 14 of the hygiene article 2 which is, however, several millimeters larger than the separation A. In further travel of the cuff base lines 34, 36 from the crotch region into the forward region 6, the separation between the cuff base lines 34, 36 increases in a continuous fashion up to a value $A_{2max}$, which is somewhat smaller than the value $A_{1max}$ and then decreases once more towards the longitudinal end 44 to the initial value A.

The cuff elements 26, 28 are thereby guided in such a fashion that the separation between the cuff base lines 34, 36 in the longitudinal direction passes through maxima which are preferentially at least partially disposed in the forward region 26 or in the rear region 8 of the hygiene article. As indicated in the current embodiment, if the distal edges 30, 32 of the cuff elements in the rear and forward regions are introduced towards the inside on the upper side of the hygiene article (cuff end attachment 82) pocket shaped barriers (45) result which, in addition to assisting in the primary function of the cuff elements of preventing sideward discharge also constitute a discharge, barrier towards the waist edges. This is particularly advantageous when, as indicated, the cuff base lines taper inwardly in a substantially even fashion towards the front end or the rear region in the region of the cuff end attachments.

The absorptive body layer 24 which serves for long term storage of body fluids, is non-homogeneous i.e. it does not have a constant surface density throughout its entire extent, rather its surface density increases in the transverse direction 44 towards the side end edges 16 and it has a region 46 of higher weight of absorptive body material which is fashioned from homogenous mixture of cellulose fibers and super-absorbing particle shaped materials. This can be seen from the section of FIG. 2. This hatched region 46 of increased surface density extends along an edge of the absorptive body and includes at least one partial region 48 (cross hatching) in which the separation between the cuff base lines 34, 36 with respect to each other is larger than outside of this partial region 48. The largest separation 42 between the cuff base lines 34, 36 or a maximum separation 42 between the cuff base lines 34, 36 is disposed in a longitudinal section of the hygiene article where the absorptive body layer 26 has a higher surface density i.e. where the region 46 is also located. The increase in the absorptive body layer 24 in the edge region leads to an increased storage capacity at those areas. This is particularly advantageous in the partial regions 48, 50 of the region 46 in that the separation 48 between the cuff base lines 34, 36 is increased. This leads to improved absorption characteristics in particular for rapid retention of body fluids. This is the case in the front regions 6 and in the rear regions 8 due to the larger increasing separation between the cuff base line 34, 36 with respect to each other and thereby allows for a larger load of fluid retaining absorbing materials which is particularly advantageous in the event of bowel incontinence in the rear region of the product. Widely extending retention regions for body discharges are created precisely in the region of the liquid barriers and are formed by the elevated cuff elements 30, 32 for increased storage capacity and increased protection with respect to sideward liquid discharge.

Figure 3:
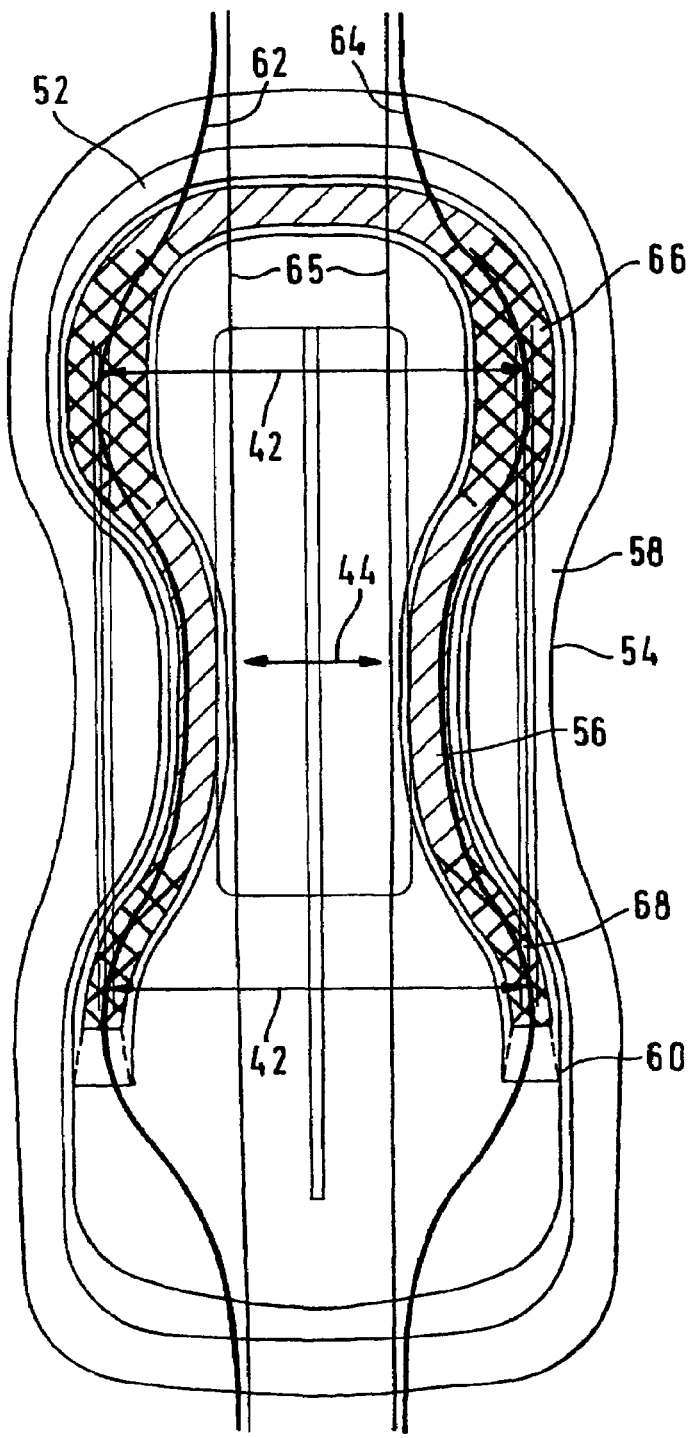
FIG. 3 shows a plan view of an absorptive body of a further embodiment with the indicated dependence of the cuff base lines.

FIG. 3 show a plan view of an absorptive body 52 of a further embodiment of the hygiene article in accordance with the invention. As with the absorptive body 24 of the hygiene article according to. FIG. 1, the absorptive body 52 has an increasing surface density in the transverse direction 44 towards the sideward longitudinal edges 54 as indicated by hatched regions 56. There is a thin fluffed layer 58 of uniform surface density which is disposed between the absorptive body layer 60 and a back sheet (not shown). Cuff elements are indicated by their cuff base lines 62, 64 and their distal end 65 and extend in the longitudinal direction with varying separations A between the cuff base lines 62, 64. Moreover, at least a partial region 66, 68 of the region 56 of increased surface density has a cuff base line separation 42 which is larger than outside of the partial region 66, 68.

In contrast to FIG. 1, the region 56 of higher surface density is closed in a ring-liked fashion in-the forward region of the absorptive body 52 (see FIG. 3). This embodiment is advantageously used in an incontinence article for men.

It has turned out to be advantageous for both embodiments when the increase in surface density is accompanied by an increased thickness of the absorptive body layer and thereby of the absorptive body. This supports the leakage properties in a region of the edge of the absorptive bodies in a highly effective manner.

FIG. 4 and 5 show a plan view as well as a section through an additional absorptive body layer 70 in accordance with the invention. In contrast to the embodiments according to FIG. 1 and 2, the overall surface density of the absorptive body layer 70 increases in the longitudinal direction 38 towards one end 72 of the hygiene article which, for its part, is not shown in FIG. 5. The increase in the thickness of the absorptive body layer 70 is effected by means of a ramp-like increase between the crotch region and the front region or the rear region of the hygiene article. One notices the region 74 of increased surface density. Also schematically shown is the travel of the cuff base lines 76, 78 and the distal ends 80 of the cuff elements. One notices that the cuff base lines 76, 78 have a maximum mutual separation which is disposed in the region 74 of increased surface density.

We claim:
1. A hygiene article for single use, the article comprising:
an absorbing body layer having means for long term storage of body fluids or super absorbing materials, said absorbing layer having a first region with a first mass per unit area of absorbing material and having at least one second region adjacent to said first region, said at least one second region having a second mass per unit area which is greater than said first mass per unit area;
a first cuff element attached to the hygiene article along a first cuff base line travelling longitudinally proximate to a first longitudinal side of the article, said first cuff element slanting upwardly and inwardly away from said first cuff base line to rise above said absorbing layer at vertical heights therefrom, said first cuff element having a first inner, distal end separated from said first cuff base line by a first cuff element length, said first cuff element length increasing in locations of said first cuff element bordering at least a partial region of said at least one second absorbing layer region; and a second cuff element attached to the hygiene article along a second cuff base line travelling longitudinally proximate to a second longitudinal side of the article, said second cuff element slanting upwardly and inwardly away from said second cuff base line to rise above said absorbing layer at vertical heights therefrom, said second cuff element having a second inner, distal end separated from said second cuff base line by a second cuff element length, said second cuff element length increasing in locations of said second cuff element bordering at least a partial region of said at least one second absorbing layer region, wherein said first and said second cuff elements define inwardly slanted walls for blocking transverse discharge, said first cuff baseline having a transverse separation from said second cuff baseline which increases at locations of said first and said second cuff elements bordering said partial region of said at least one second absorbing layer region, wherein said partial region is disposed outside of a middle, longitudinal section in a forward region and/or in a rear region of the hygiene article.

2. The hygiene article of claim 1, wherein said cuff elements extend in such a fashion that said separation between said cuff base lines along said longitudinal direction has at least one maximum.

3. The hygiene article of claim 2, wherein said maximum is completely within said partial region.

4. The hygiene article of claim 1, wherein said absorbing body layer includes a mixture of fibers and particle shaped super-absorbing materials.

5. The hygiene article of claim 1, wherein said cuff base lines of said cuff elements extend along both sides and join onto each other in a forward region and/or backward region.

6. The hygiene article of claim 1, wherein said cuff base lines of said cuff elements extend along both sides and are separated from each other at a longitudinal end of a forward and/or of a backward region.

7. The hygiene article of claim 1, wherein said separation between said cuff base lines in a middle, longitudinal section of the hygiene article and outside of said partial region is 130 to 170 mm.

8. The hygiene article of claim 1, wherein said separation between said cuff base lines in a middle longitudinal section of the hygiene article and outside of said partial region is 140 to 165 mm.

9. The hygiene article of claim 1, wherein said separation between said cuff base lines in said partial region is 160-220 mm.

10. The hygiene article of claim 1, wherein said separation between said cuff base lines in said partial region is 180-200 mm.

11. The hygiene article of claim 1, wherein said separation between said cuff base lines in said partial region is 185-195 mm.

12. The hygiene article of claim 1, wherein said separation between said cuff base lines in an end region including a longitudinal end of the hygiene article assumes values of 100-180 mm.

13. The hygiene article of claim 1, wherein a mass per unit area of said absorbing body layer or of said absorbing material increases in a transverse or in a longitudinal direction by 30-200%.

14. The hygiene article of claim 1, wherein said mass per unit area of said absorbing material in said absorbing body layer outside of said partial region is 200-500 $g/m^2$.

15. The hygiene article of claim 1, wherein said mass per unit area of said absorbing material of said absorbing body layer inside of said partial region is 250-1000 $g/m^2$.

16. The hygiene article of claim 1, wherein said first and second cuff element length within said partial region is 40-60 mm.

17. The hygiene article of claim 1, wherein said first and second cuff element length outside of said partial region is 30-40 mm.

* * * * *